United States Patent [19]

Firestone et al.

[11] Patent Number: 4,680,391

[45] Date of Patent: Jul. 14, 1987

[54] SUBSTITUTED AZETIDINONES AS ANTI-INFLAMMATORY AND ANTIDEGENERATIVE AGENTS

[75] Inventors: Raymond A. Firestone, Fanwood; Peter L. Barker, Westfield, both of N.J.

[73] Assignee: Merck & Co., Inc., Rahway, N.J.

[21] Appl. No.: 721,811

[22] Filed: Apr. 10, 1985

Related U.S. Application Data

[63] Continuation-in-part of Ser. No. 557,030, Dec. 1, 1983, abandoned.

[51] Int. Cl.⁴ .................. C07D 205/08; C07D 401/04; C07D 403/04; A61K 31/395

[52] U.S. Cl. .................. 540/355; 540/200; 540/354; 540/359; 540/360; 540/361; 540/362; 540/363; 540/364; 540/357

[58] Field of Search .................. 260/239 A

[56] References Cited

U.S. PATENT DOCUMENTS 4,550,105 10/1985 Matsuo .................. 540/355

Primary Examiner—Mark L. Berch
Attorney, Agent, or Firm—Theresa Y. Cheng; Michael C. Sudol

[57] ABSTRACT

New substituted azetidinones are found to be potent elastase inhibitors and thereby useful anti-inflammatory-/antidegenerative agents.

11 Claims, No Drawings

SUBSTITUTED AZETIDINONES AS ANTI-INFLAMMATORY AND ANTIDEGENERATIVE AGENTS

This is a continuation-in-part application of copending application Ser. No. 557,030 filed Dec. 1, 1983, abandoned.

BACKGROUND OF THE INVENTION

We have found that a group of new substituted azetidinones are potent elastase inhibitors and therefore are useful anti-inflammatory/antidegenerative agents.

Proteases from granulocytes and macrophages have been reported to be responsible for the chronic tissue destruction mechanisms associated with inflammation, including rheumatoid arthritis and emphysema. Accordingly, specific and selective inhibitors of these proteases are candidates for potent anti-inflammatory agents useful in the treatment of inflammatory conditions resulting in connective tissue destruction, e.g., rheumatoid arthritis, emphysema, bronchial inflammation, osteoarthritis, spondylitis, lupus, psoriasis and acute respiratory distress syndrome.

The role of proteases from granulocytes, leukocytes or macrophages are related to a rapid series of events which occurs during the progression of an inflammatory condition:

(1) There is a rapid production of prostaglandins (PG) and related compounds synthesized from arachidonic acid. This PG synthesis has been shown to be inhibited by aspirin-related nonsteroidal anti-inflammatory agents including indomethacin and phenylbutazone. There is some evidence that protease inhibitors prevent PG production;

(2) There is also a change in vascular permeability which causes a leakage of fluid into the inflamed site and the resulting edema is generally used as a marker for measuring the degree of inflammation. This process has been found to be induced by the proteolytic or peptide cleaving activity of proteases, especially those contained in the granulocyte, and thereby can be inhibited by various synthetic protease inhibitors, for example, N-acyl benzisothiazolones and the respective 1,1-dioxides. Morris Zimmerman et al., *J. Biol. Chem.*, 255, 9848 (1980); and (3) There is an appearance and/or presence of lymphoid cells, especially macrophages and polymorphonuclear leukocytes (PMN). It has been known that a variety of proteases are released from the macrophages and PMN, further indicating that the proteases do play an important role in inflammation.

In general, proteases are an important family of enzymes within the peptide bond cleaving enzymes whose members are essential to a variety of normal biological activities, such as digestion, formation and dissolution of blood clots, the formation of active forms of hormones, the immune reaction to foreign cells and organisms, etc., and in pathological conditions such as the degradation of structural proteins at the articular cartilage/pannus junction in rheumatoid arthritis etc.

Elastase is one of the proteases. It is an enzyme capable of hydrolyzing the connective tissue component elastin, a property not contained by the bulk of the proteases present in mammals. It acts on a protein's nonterminal bonds which are adjacent to an aliphatic amino acid. Neutrophil elastase is of particular interest because it has the broadest spectrum of activity against natural connective tissue substrates. In particular, the elastase of the granulocyte is important because, as described above, granulocytes participate in acute inflammation and in acute exacerbation of chronic forms of inflammation which characterize many clinically important inflammatory diseases.

Proteases may be inactivated by inhibitors which block the active site of the enzyme by binding tightly thereto. Naturally occuring protease inhibitors form part of the control or defense mechanisms that are crucial to the well-being of an organism. Without these control mechanisms, the proteases would destroy any protein within reach. The naturally occurring enzyme inhibitors have been shown to have appropriate configurations which allow them to bind tightly to the enzyme. This configuration is part of the reason that inhibitors bind to the enzyme so tightly (see Shroud, "A Family of Protein-Cutting Proteins" *Sci. Am.* July 1974, pp. 74–88). For example, one of the natural inhibitors, $\alpha_1$-Antitrypsin, is a glycoprotein contained in human serum that has a wide inhibitory spectrum covering, among other enzymes, elastase both from the pancrease and the PMN. This inhibitor is hydrolyzed by the proteases to form a stable acyl enzyme in which the active site is no longer available. Marked reduction in serum $\alpha_1$-antitrypsin, either genetic or due to oxidants, has been associated with pulmonary emphysema which is a disease characterized by a progressive loss of lung elasticity and resulting respiratory difficulty. It has been reported that this loss of lung elasticity is caused by the progressive, uncontrolled proteolysis or destruction of the structure of lung tissue by proteases such as elastase released from leukocytes. J. C. Powers, *TIBS*, 211 (1976).

Rheumatoid arthritis is characterized by a progressive destruction of articular cartilage both on the free surface bordering the joint space and at the erosion front built up by synovial tissue toward the cartilage. This destruction process, in turn, is attributed to the protein-cutting enzyme elastase which is a neutral protease present in human granulocytes. This conclusion has been supported by the following observations:

(1) Recent histochemical investigations showed the accumulation of granulocytes at the cartilage/pannus junction in rheumatoid arthritis; and (2) a recent investigation of mechanical behavior of cartilage in response to attack by purified elastase demonstrated the direct participation of granulocyte enzymes, especially elastase, in rheumatoid cartilage destruction. H. Menninger et al., in *Biological Functions of Proteinases*, H. Holzer and H. Tschesche, eds. Springer-Verlag, Berlin, Heidelberg, New York, pp. 196–206, 1979.

Accordingly, an object of this invention is to discover new protease inhibitors, especially elastase inhibitors, useful for controlling tissue damage and various inflammatory or degenerative conditions mediated by proteases particularly elastase.

Another object of the present invention is to provide pharmaceutical compositions for administering the active substituted azetidinones as protease inhibitors especially human leukocyte elastase.

Still a further object of this invention is to provide a method of controlling inflammatory conditions by administering a sufficient amount of one or more of the active, substituted azetidinones in a mammalian species in need of such treatment.

DETAILED DESCRIPTION OF THE INVENTION

This invention relates to potent elastase inhibitors of formula (I) which are useful in the prevention, control and treatment of inflammatory/degenerative conditions especially arthritis and emphysema.

A large number of the azetidinone derivatives of formula (I) are known antibiotics which have been described in patents and various publications.

The formula of the substituted azetidinones which are found to exhibit anti-inflammatory and antidegenerative activities by the present invention are represented as follows:

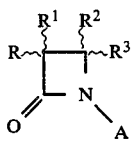 (I)

wherein

R can be at the α-or the β-position and is hydrogen, loweralkyl especially $C_{1-6}$alkyl, such as methyl, ethyl, n- or i-propyl, butyl, pentyl or hexyl; or halo such as fluoro, chloro or bromo;

$R^1$ can be at the α- or the β-position and is
 (1) $OR^4$ wherein $R^4$ represents
(a) H;
(b) Straight or branched loweralkyl group especially $C_{1-6}$alkyl;
 (2) Straight or branched loweralkenyl group especially $C_{2-8}$alkylenyl such as vinyl, allyl, —CH₂CH=C(CH₃)₂, and —CH₂CH₂CH=CH₂;
 (3) loweralkyl as defined above;
 (4) acylamino e.g.

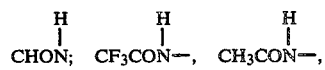 CHON; CF₃CON—, CH₃CON—,

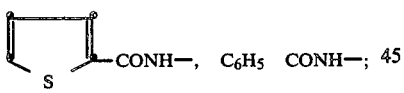 —CONH—, C₆H₅ CONH—;

or
 (5) amino;
 (6) Straight or branched loweralkynyl group especially $C_{3-6}$alkynyl such as —C≡CH, —CH₂—C≡CH and —CH₂CH₂—C≡CCH₃;
 (7) An aryl group having 6–10 carbon atoms as described below such as unsubstituted or substituted phenyl, for example phenyl, p-methoxyphenyl, m-aminosulfonylphenyl;
 (8) heteroaryl such as unsubstituted or substituted furyl, thienyl, thiazolyl, pyrryl, pyrimidinyl, pyridyl, oxazolyl or imidazolyl which substituents are as those described for substituted phenyls;
 (9) aralkyl especially phenyl $C_{1-6}$alkyl such as benzyl, phenethyl or p-methoxybenzyl;
 (10) halogen such as F, Cl, Br or I;
 (11) N₃; or
 (12) hydrogen;

$R^2$ and $R^3$ can be at the α- or the β-position and are independently (1) hydrogen;
 (2) $SR^5$ wherein $R^5$ represents $C_{1-6}$alkyl, or aryl as previously defined, e.g., substituted or unsubstituted phenyl such as p-nitrophenyl, p-methylphenyl or 2-pyrimidinyl;
 (3) $SOR^5$;
 (4) $SO_2R^5$;
 (5) halo;
 (6) —COOB or —CONBB₁ wherein B and B₁ independently represent
  (a) H;
  (b) straight or branched alkyl having from 1 to 20 carbon atoms, preferably $C_{1-6}$alkyl such as methyl, ethyl, isopropyl, t-butyl, pentyl or hexyl;
  (c) aryl having from 6 to 10 carbon atoms;
  (d) cycloalkyl having from 3 to 8 carbon atoms especially cyclopropyl, cyclopentyl or cyclohexyl;
  (e) straight or branched alkenyl having from 2 to 20 carbon atoms;
  (f) straight or branched alkynyl having from 2 to 20 carbon atoms;
  (g) aralkyl, alkaryl, aralkenyl, aralkenyl, alkenylaryl or alkenylaryl wherein alkyl, aryl, alkenyl and alkynyl are as previously defined;
 the above groups (a)–(g) can be unsubstituted or can be substituted by radicals such as alkyl, hydroxy, alkoxy, halo, nitro, loweralkylthio, arylthio, mercapto, amino, substituted amino, cyano, carboxy, aminosulfonyl, aminosulfenyl, aminosulfinyl, carbamoyl, carbamoyloxy, loweralkyl or aryl sulfonyl, loweralkyl or aryl sulfinyl, $SO_3R^5$, azido, amino, substituted amino, carboxamido or N-substituted carboxamido; and
 (7) lower alkanoyl especially $C_{1-6}$alkanoyl such as acetyl;
 (8) aroyl especially benzoyl or substituted benzoyl, for example p-chlorobenzoyl, p-methylphenyl or p-aminosulfonylbenzoyl;
 (9) aryl as defined above especially phenyl or substituted phenyl;
 (10) loweralkanoyloxy especially $C_{1-6}$alkanoyloxy such as acetyloxy;
 (11) cyano;
 (12) loweralkanoylthio especially $C_{1-6}$alkanoylthio such as acetylthio;
 (13) H; or
 (14) loweralkenyl especially $C_{1-6}$alkenyl such as allyl;

A is
 (1) $SR^5$;
 (2) $SOR^5$;
 (3) $SO_2R^5$;
 (4) loweralkanoyl as previously defined;
 (5) $SO_3$-M⁺ where in M represents
  (a) an alkali anion such as Na⁺, K⁺; or
  (b) a quaternary ammonium group of formula $N^+(R^5)_4$, for example, (n-Bu)₄N⁺;
 (6) substituted or unsubstituted phosphate or phosphonyl;
 (7) aroyl as defined previously;
 (8) loweralkoxycarbonyl especially $C_{1-6}$alkoxycarbonyl, e.g., methoxycarbonyl, exthoxycarbonyl;
 (9) halo $C_{1-6}$alkyl such as trifluoromethyl;
 (10) halo;
 (11) hydrogen;
 (12) phenyl or substituted phenyl as defined previously;

(13)

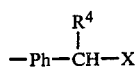

where R[4] and X are as defined below;

(14) O—CH$_2$-substituted or unsubstituted phenyl for example, —OCH$_2$C$_6$H$_5$; —OCH$_2$—C$_6$H$_4$—OCH$_3$; or OCH$_2$C$_6$H$_4$NO$_2$;
(15) silyl such as —Si(CH$_3$)$_2$(t-Bu);
(16) tetrazolyl, for example,

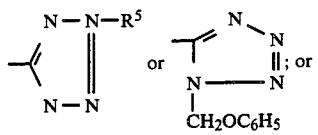

or

(17) CHR[4]X where R[4] represents H, aryl or lower alkyl and X is a good leaving group comprising OAc, SAc, halogen, OR[5], SR[5], SOR[5], SO$_2$R[5], OTs, OCOCF$_3$, and mesyl wherein Ac is acetyl; and Ts is tosyl.

Preferably, the compounds of the present invention are of formula (I) wherein;

R is hydrogen; or loweralkyl;
R[1] is
(1) OR[4];
(2) C$_{1-6}$alkyl;
(3) C$_{2-8}$alkenyl;
(4) hydrogen;
(5) azido (N$_3$);
(6) chloro or fluoro; or
(7) phenyl or substituted phenyl;
R[2] and R[3] independently are
(1) hydrogen;
(2) SOR[5];
(3) SR[5];
(4) COOB;
(5) C$_{1-6}$alkanoyloxy such as acetyloxy;
(6) C$_{1-6}$alkanoylthio such as acetylthio; or
(7) C$_{2-8}$alkenyl; and
A is
(1) SOR[5];
(2) SO$_2$R[5];
(3) —CHR[4]X;
(4) C$_{1-6}$alkanoyl such as acetyl;
(5) SO$_3^-$M$^+$;
(6) substituted or unsubstituted phenyl such as p-methoxyphenyl, p-nitrophenyl and p-methylphenyl.

Even more preferably, the compounds of the present invention are of formula (I) wherein R is hydrogen or C$_{1-3}$alkyl;

R[1] is
(1) hydrogen;
(2) C$_{1-6}$alkyl;
(3) C$_{1-6}$alkoxy such as methoxy;
(4) C$_{1-6}$alkenyl; or
(5) substituted or unsubstituted phenyl;
R[2] is hydrogen;
R[3] is
(1) SOR[5];
(2) SR[5];
(3) C$_{1-6}$-alkanoyloxy such as acetyloxy;
(4) COOB; or
(5) substituted or unsubstituted phenyl; and A is
(1) C$_{1-6}$-alkanoyl such as acetyl;
(2) hydrogen;
(3) SO$_2$R[5];
(4) —CH$_2$OAc; or
(5) SO$_3^-$m$^+$.

The compounds of the present invention are either known or are prepared among other methods by the following representative schemes.

Scheme (a) as illustrated by Examples 16–19.

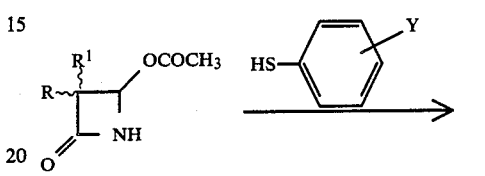

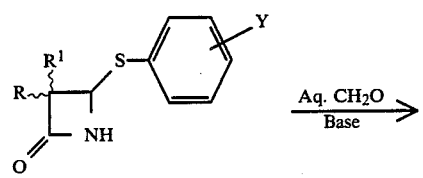

(A)

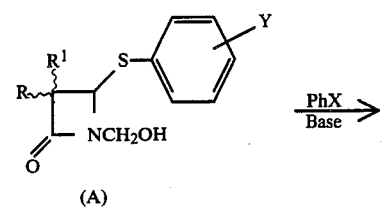

(B)

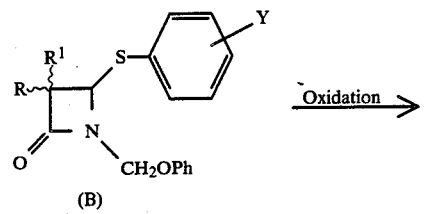

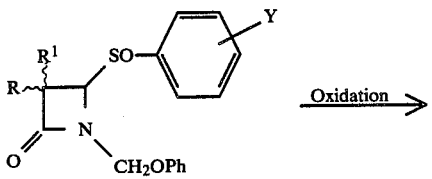

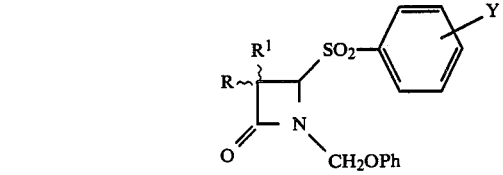

wherein
Y is —NO$_2$, —CH$_3$, —OCH$_3$, —Cl, —F, etc;
X is halo, e.g., Cl, Br or I;
ph is substituted or unsubstituted phenyl as previously defined.

Scheme (b) as illustrated by Examples 1–4.

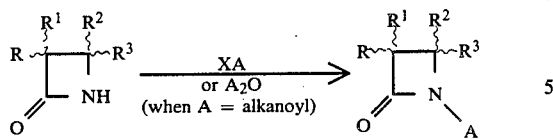
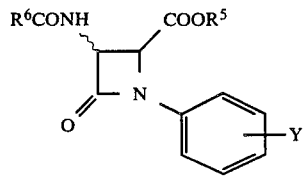

wherein
X is halo;
A is as previously defined, e.g., —SO$_2$—(-p—NO$_2$—ph), —COCH$_3$, —CH$_2$OTs, etc. wherein ph represents substituted or unsubstituted ph.
Scheme (c) as illustrated by Examples 5–15

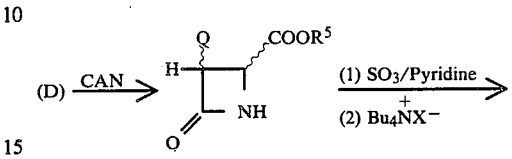

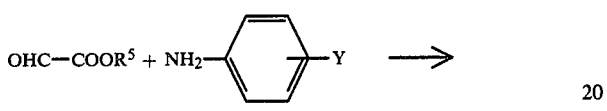

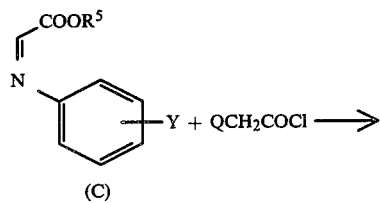

(C)

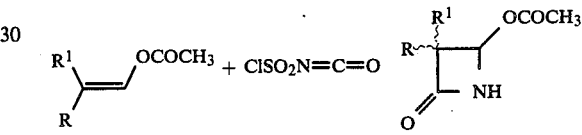

wherein
R$^6$ is H, CF$_3$, CH$_3$, etc.;
Y is as previously defined; and
CAN is cerric ammonium nitrate.
Scheme (d) as illustrated by Examples 2–3.

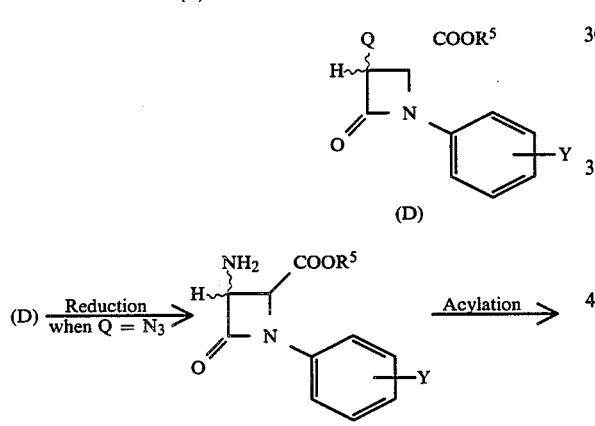

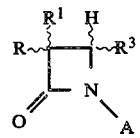

(D)

This invention also relates to a method of treating inflammation in patients using a compound of Formula (I), particularly an especially preferred compound as the active constituent.

It has been found that the compounds of Formula (I) have anti-inflammatory and/or anti-degeneration activity and are effective in the prevention and inhibition of edema and granuloma tissue formation as shown below in Table I by the effective inhibition of the proteolytic function of human granulocyte elastase.

TABLE I

| R | R$^1$ | R$^3$ | A | IC$_{50}$ ( g/ml) |
|---|---|---|---|---|
| H | H | SOCH$_3$ | COCH$_3$ | 10 |
| H | H | OCOCH$_3$ | COCH$_3$ | 3 |
| H | C$_2$H$_5$ | OCOCH$_3$ | H | 15 |
| H | C$_2$H$_5$ | OCOCH$_3$ | COCH$_3$ | 0.1 |
| H | n-propyl | OCOCH$_3$ | COCH$_3$ | 0.01 |
| H | C$_6$H$_5$(trans) | COOC$_2$H$_5$ | H | 10 |
| H | H | COOCH$_2$C$_6$H$_5$ | SO$_2$(p-C$_6$H$_5$—NO$_2$) | 3 |
| CH$_3$ | CH$_3$ | OCOCH$_3$ | COCH$_3$ | 0.5 |
| H | C$_6$H$_5$(trans) | COOC$_2$H$_5$ | SO$_2$(p-C$_6$H$_5$—NO$_2$) | 4 |
| H | C$_6$H$_5$(cis) | COOC$_2$H$_5$ | SO$_2$(p-C$_6$H$_5$—NO$_2$)$_2$ | 3 |
| H | n-C$_3$H$_5$— | OCOCH$_3$ | SO$_3^-$(Bu)$_4$N$^+$ | 8 |
| H | CH$_2$=CH—(cis) | COOC$_2$H$_5$ | SO$_2$(p-C$_6$H$_4$NO$_2$) | 0.02 |
| H | C$_2$H$_5$—(cis) | COOC$_2$H$_5$ | SO$_2$(p-C$_6$H$_4$NO$_2$) | 0.05 |
| H | C$_2$H$_5$—(trans) | COOC$_2$H$_5$ | SO$_2$(p-C$_6$H$_4$NO$_2$) | 0.01 |
| H | C$_2$H$_5$—(trans) | COOC$_2$H$_5$ | SO$_2$(p-C$_6$H$_4$CH$_3$) | 0.01 |

TABLE I-continued $$\underset{O}{\overset{R^1}{\underset{R\sim}{\vphantom{|}}}}\overset{H}{\underset{\vphantom{|}}{\vphantom{|}}}\text{-}R^3$$
(azetidinone with N-A)

| R | R$^1$ | R$^3$ | A | IC$_{50}$ ($\mu$g/ml) |
|---|---|---|---|---|
| H | n-C$_3$H$_5$—(cis) | COOC$_2$H$_5$ | SO$_2$(p-C$_6$H$_4$NO$_2$) | 0.06 |
| H | CH$_3$CH$_2$=CH—(cis) | COOC$_2$H$_5$ | SO$_2$(p-C$_6$H$_4$NO$_2$) | 0.05 |
| H | CH$_2$=CH— | p-(C$_6$H$_4$—NO$_2$)— | H | 1.5 |

Protocol—Enzyme Assays for the Inhibition of Human Polymorphonuclear Leukocyte Elastase Via Hydrolysis of N-t-Boc-alanyl-alanyl-prolylalanine-p-nitroanilide Reagents:

0.05M TES (N-tri[hydroxymethyl]methyl-2-aminoethanesulfonic acid) Buffer, pH 7.5.

0.2 mM N-t-Boc-alanyl-alanyl-propyl-alanine-p-nitroanilide (Boc-AAPAN).

To prepare substrate, the solid (m.w. 550) was first dissolved in 10.0 ml DMSO. Buffer at pH 7.5 was then added to a final volume of 100 ml.

Crude extract of human polymorphonuclear leukocytes (PMN) containing elastase activity.

Inhibitors (azetidines) to be tested dissolved in DMSO just before use.

Assay Procedure:

To 1.0 ml of 0.2 mM Boc-AAPAN in a cuvette, 0.01–0.1 ml of DMSO with or without inhibitor was added. After mixing, a measurement was taken at 410 m$\mu$ to detect any spontaneous hydrolysis due to presence of test compound. 0.05 Milliliters of PMN extract was then added and the $\Delta$OD/min at 410 m$\mu$ was measured and recorded. Beckman model 35 spectrophotometer was used.

Results:

Results were reported as IC$_{50}$, i.e., effective dosage in micrograms per milliliter ($\mu$g/ml) for 50% inhibition of the enzyme activity 2 minutes after zero time.

Comments:

The elastase activity in the crude PMN extract may vary from one preparation to another. A control of each new batch is run, and the volume added in the assay procedure is adjusted according to activity.

Accordingly, the compounds of Formula (I) can be used to reduce inflammation and relieve pain in diseases such as emphysema, rheumatoid arthritis, osteoarthritis, gout, bonchial inflammation, infectious arthritis, rheumatic fever and the like.

For treatment of inflammation, fever or pain, the compounds of Formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cts, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets contain the active ingredient in admixture with non-toxic pharmaceutically acceptable excipients which are suitable for the manufacture of tablets. These excipients my be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients aare suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin of cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the anti-inflammatory agents are employed.

Dosage levels of the order to 0.2 mg to 140 mg per kilogram of body weight per day are useful in the treatment of the above-indicated conditions (10 mg to 7 gms. per patient per day). For example, inflammation is effectively treated and anti-pyretic and analgesic activity manifested by the administration from about 0.5 to 50 mg of the compound per kilogram of body weight per day (25 mg to 3.5 gms per patient per day). Advantageously, from about 2 mg to about 20 mg per kilogram of body weight per daily dosage produces highly effective results (50 mg to 1 gm per patient per day).

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

EXAMPLE 1

1-p-nitrophenylsulfonyl-4-benzyloxycarbonyl azetidin-2-one

Diazabicycloundecane (152 mg, 1 mM) was added to a mixture of 205 mg (1 mM) azetidinone and 181 mg (1 mM) p-nitrobenzenesulfonyl chloride in 10 ml methylene chloride at room temperature. After stirring 2½ hours, the orange solution was washed with water, dried over $MgSO_4$, and concentrated in vacuo. The residue was chromatographed on silica gel in hexane/ethyl acetate to yield 64 mg (17%) of 1-p-nitrophenylsulfonyl-4-benzyloxycarbonyl azetidin-2-one.

NMR ($CDCl_3$): δ 3.3 (2H, doublet-quartet), 4.8 (qt. 1H), 5.2 (s, 2H), 7.2 (s, 5H), 8.2 (mlt. 4H).

EXAMPLE 2

1-Acetyl-3,3-dimethyl-4-acetoxyazetidin-2-one

Step A: Preparation of 2-methyl-prop-1-enylacetate

A mixture of 72 g (1m) isobutyraldehyde, 153 g (1.5m) acetic anhydride and 12 g (0.125M) potassium acetate was refluxed seven hours. The cooled reaction mixture was washed with water and stirred with 300 ml saturated $NaHCO_3$ at 0° C. for 45 minutes. The organic phase was dried over $K_2CO_3$ to yield a yellow oil which was distilled at atmospheric pressure to give 35.41 g (31%) of 2-methyl-prop-1-enylacetate, b.p. 122°–126°.

NMR ($CDCl_3$): δ1.6 (s, 6H), 2.1 (s, 3H), 6.9 (mlt. 1H).

Step B: Preparation of 3-3-dimethyl-4-acetoxyazetidin-2-one

Chlorosulfonyl isocyanate (16 ml) was added to a solution of 22.8 g (0.2M) 2-methyl prop-1-enyl acetate in 50 ml methylene chloride at 0° under nitrogen. After stirring at 0° for 20 hours, the reaction mixture was added to a mixture of 20 ml water, 90 g ice, 48 g $NaHCO_3$ and 16.6 g $Na_2SO_3$ and stirred at 0° for 30 minutes. This was then extracted with 300 ml $CH_2Cl_2$ and the organic phase washed with brine, dried over $MgSO_4$ and concentrated in vacuo to give 27.75 g oil which was chromatographed on silica gel in hexane/ethyl acetate to yield 2.17 g (8.5%) of 3,3-dimethyl-4-acetoxyazetidin-2-one.

NMR (CDCl$_3$): δ 1.2 (s, 3H), 1.3 (s, 3H), 2.2 (s, 3H), 5.6 (s, 1H).

Step C: Preparation of 1-acetyl-3,3-dimethyl-4-acetoxyazetidin-2-one

A mixture of 283.3 mg (1.8 mM) 3,3-dimethyl-4-acetoxyazetidin-2-one, 2 ml pyridine and 2 ml acetic anhydride was heated to 100° in a sealed tube for 36 hours. The reaction mixture was concentrated in vacuo and the residue chromatographed on silica gel in hexane/ethyl acetate to yield 295 mg (82%) of 1-acetyl-3,3-dimethyl-4-acetoxyazetidin-2-one.

NMR (CDCl$_3$): δ 1.2 (s, 3H), 22 (s, 3H), 2.5 (s, 3H), 6.1 (s, 1H).

EXAMPLE 3

1-Acetyl-4-acetoxy-3-n-propylazitidin-2-one

Step A: Preparation of Pent-1-enyl acetate

A mixture of 86 g (1m) valeraldehyde, 153 g (1.5M) acetic anhydride, and 12 g (0.125M) potassium acetate, was refluxed for 8 hours. The cooled mixture was then stirred with 100 ml saturated aqueous NaHCO$_3$ for one hour. The organic phase is separated, dried over K$_2$CO$_3$, and distilled at 40 mm to yield 46.15 g (45%) of pent-1-enylacetate, b.p. 89° C.

NMR (CDCl$_3$): δ 1.0 (tr, 3H), 1.2–2.0 (mlt., 4H), 2.1 (s, 3H), 4.7–5.6 (mlt. 1H), 7.0–7.3 (mlt., 1H).

Step B: Preparation of 4-acetoxy-3-n-propylazetidin-2-one

Eight hundred microliters of chlorosulfonyl isocyanate was added to a solution of 1.28 g (10 mM) pent-1-enyl acetate in 5 ml methylene chloride at 0° under nitrogen. After stirring at 0° 5 days, the reaction mixture was added dropwise to a mixture of 5 g ice, 1.15 ml water, 2.82 g NaHCO$_3$ and 1.0 g Na$_2$SO$_3$ and stirred at 0° for 30 minutes. The mixture was extracted with 2×25 ml methylene choride and the combined organic phases washed with brine, dried over MgSO$_4$, and concentrated in vacuo. The residue was chromatographed on silica gel in hexane/ethyl acetate to yield 60 mg trans 4-acetoxy-3-n-propylazetidin-2-one (3.4%).

NMR (CDCl$_3$): δ 1.0 (mlt., 3H), 1.7 (mlt., 4H), 2.2 (s, 3H), 3.2 (tr, 1H), 5.6 (s, 1H), 6.7 (1 rs, 1H).

Step C: Preparation of 1-acetyl-4-acetoxy-3-n-propyl-azetidine-2-one

A mixture of 56 mg (0.33 mM) 4-acetoxy-3-propylazetidin-2-one, 1 ml acetic anhydride and 1 ml pyridine was stirred at 100° in a sealed tube for 24 hours. After concentrating in vacuo the residue was chromatographed on silica gel in hexane/ethyl acetate, to yield 16 mg (23%) 1-acetyl-4-acetoxy-3-n-propyl-azetidine-2-one.

NMR (CDCl$_3$): δ 1.0 (br tr, 3H), 1.7 (mlt., 4H), 2.2 (s, 3H), 2.4 (s, 3H), 3.2 (tr, 1H), 6.1 (d, 1H).

EXAMPLE 4

1-Acetyl-4-methylsulfonylazetidin-2-one

Step A: Preparation of 1-acetyl-4-methylthioazetidin-2-one

A mixture of 300 mg (2.6 mM) 4-methylthioazetidin-2-one, 10 ml acetic anhydride and 10 ml pyridine was stirred at 100° in a sealed tube 24 hours. After concentrating in vacuo, the residue was chromatographed on silica gel in hexane/ethyl acetate to yield 324 mg (78%) of 1-acetyl-4-methylthioazetidine-2-one.

NMR (CDCl$_3$): δ 2.4 (s, 3H), 2.41 (s, 3H), 3.2 (doublet-quartet, 2H), 5.1 (doublet-doublet, 1H).

Step B: Preparation of N-acetyl-4-methylsulfinylazetidin-2-one

A mixture of 130 mg (0.82 mM) N-acetyl-4-methylthioazetidinone and 200 mg (0.93 nM) 80% m-chloroperbenzoic acid in 5 ml methylene chloride was stirred at room temperature 5 minutes. After removing the solvent in vacuo. The residue was chromatographed on 2–2000μ silica gel plates in hexane/ethyl acetate to yield 57 mg (40%) of 1-acetyl-4-methylsulfinylazetidine-2-one.

NMR (CDCl$_3$): δ 2.4 (s, 3H), 2.6 (s, 3H), 3.5 (mlt., 2H), 4.9 (mlt., 1H).

EXAMPLE 5

3-Azido-4-carboethoxy-1-(p-methoxyphenyl)azetidin-2-one

To a solution of 3.06 g of azidoacetyl chloride in 50 ml of CH$_2$Cl$_2$ was added dropwise a solution of 3.57 ml of triethylamine and 5.3 g of the imine formed from ethylglyoxalate and p-anisidine in 50 ml CH$_2$Cl$_2$, with cooling at such a rate that the reaction temperature remained below 5°. The reaction was then stirred at room temperature for three hours and then washed sequentially with 1H HCl, saturated aqueous sodium bicarbonate, and saturated aqueous sodium chloride. The organic phase was dried over magnesium sulfate, filtered, and evaporated, and the crude residue was recrystallized from carbon tetrachloride/hexane to afford 3.7 g. of 3-azido-4-carboethoxy-1-(p-methoxyphenyl)azetidine-2-one; m.p. 80°–85°.

NMR (CDCl$_3$): δ 7.2 (d, J=9, 2H), 6.75 (d, J=9, 2H), 4.9 (d, J=6, 1H), 4.6 (d, J=6, 1H), 4.25 (q, J=8, 2H), 3.7 (s, 3H), 1.25 (t, J=8, 3H).

EXAMPLE 6

4-Carboethoxy-3-chloro-1-(p-methoxyphenyl)azetidine-2-one 4-carboethoxy-3-chloro-1-(p-methoxyphenyl)azetidine-2-one was prepared by following the same procedure as described in Example 5 but using chloroacetyl chloride and the imine formed from ethylglyoxalate and p-anisidine as the starting material. The crude product was recrystallized from ether (hexane) to give 3.1 g of 4-carboethoxy-3-chloro-1-(p-methoxyphenyl)azetidine-2-one, m.p. 99°–100°.

NMR (CDCl$_3$): δ 7.2 (d, J=9, 2H), 6.8 (d, J=9, 2H), 5.1 (d, J=6, 1H), 4.7 (d, J=6, 1H), 4.25 (q, J=7, 2H), 3.7 (s, 3H), 1.25 (t, J=7, 3H).

EXAMPLE 7

4-Carboethoxy-3-methoxy-1-(p-methoxyphenyl)azetidine-2-one

4-Carboethoxy-3-methoxy-1-(p-methoxyphenyl)azetidine-2-one was prepared by following the same procedure as described in Example 5 but using methoxyacetyl chloride as the starting material. After chromatography the compound crystallized as a white solid: m.p. 116°–118°.

NMR (CDCl$_3$): δ 7.2 (d, J=9, 2H), 6.75 (d, J=9, 2H), 4.7 (d, J=5, 1H), 4.6 (d, J=5, 1H), 4.2 (q, J=5, 2H), 3.7 (s, 3H), 3.5 (s, 3H), 1.2 (t, J=5, 3H).

EXAMPLE 8

4-Carboethoxy-1-(p-methoxyphenyl)-3-phenylazetidin-2-one

To a solution of 17 ml of triethylamine and 5.0 g of the imine formed from ethyl glyoxalate and p-anisidine in 100 ml of refluxing 1,2-dichloroethane was added dropwise over 2 hours a solution of 16 ml of freshly distilled phenylacetyl chloride in 50 ml of dichloroethane. After refluxing for three hours the reaction was worked-up as per the 3-azidoazetidine. The crude residue was chromatographed to yield the cis and trans isomers of 4-carboethoxy-1-(p-methoxyphenyl)-3-phenylazetidin-2-one as oils; cis: NMR (CDCl$_3$): δ 7.2 (m, 7H), 6.7 (d, J=9, 2H), 4.7 (s, 2H), 3.6 (s, 3H), 3.6 (q, J=7, 2H), 0.7 (t, J=7, 3H); trans: NMR (CDCl$_3$): 7.3 (m, 7H), 6.8 (d, J=9, 2H), 4.5 (d, J=2, 1H), 4.45 (d, J=2, 1H), 4.1 (q, J=7, 2H), 3.6 (s, 3H), 1.2 (t, J=7, 3H).

EXAMPLE 9

4-Carboethoxy-1-(p-methoxyphenyl)-3-vinylazetidin-2-one

4-Carboethoxy-1-(p-methoxyphenyl)-3-vinylazetidine-2-one was prepared by following the same procedure as described in Example 8 but using crotonyl chloride as the reagent. After chromatography the cis and trans isomers of the compound were obtained; cis (m.p. 70°–72°), NMR (CDCl$_3$): δ=7.2 (d, J=9, 2H), 6.8 (d, J=9, 2H), 5.2–5.8 (m, 3H), 4.6 (d, J=6, 1H), 4.2 (m, 3H), 3.7 (s, 3H), 1.2 (t, J=7, 3H); trans (oil), NMR (CDCl$_3$): 7.25 (d, J=9, 2H), 6.8 (d, J=9, 2H), 5.7–6.2 (m, 1H), 5.2–5.5 (m, 2H), 4.25 (br.s., 1H), 4.2 (q, J=7, 2H), 3.9 (dd, J=1, Jz=6, 1H), 3.75 (s, 1H), 1.25 (t, J=7, 3H).

EXAMPLE 10

4-Carboethoxy-3-ethyl-1-(p-methoxyphenyl)azetidin-2-one

The cis and trans isomers of 4-carboethoxy-3-ethyl-1-(p-methoxyphenyl)azetidine-2-one are each hydrogenated with palladium on carbon in ethanol to yield the corresponding cis and trans isomers of 4-carboethoxy-3-ethyl-1-(p-methoxy-phenyl)azetidine-2-one.

EXAMPLE 11

4-Carboethoxy-1-(p-methoxyphenyl)-3-(N-methyl-trifluoroacetamido)azetidin-2-one

A solution of 2.16 g of 3-azido-4-carboethoxy-1-(p-methoxyphenyl)-azetidine-2-one in ethanol was hydrogenated with palladium to yield 4-carboethoxy-1-(p-methoxyphenyl)-3-aminoazetidin-2-one. This amine was acylated with 1.1 ml of trifluoro acetic anhydride in 10 ml CH$_2$Cl$_2$ containing 1.5 ml pyridine, followed by methylation using 1 ml dimethyl sulfate in 30 ml acetone containing 3 g potassium carbonate. After isolation, the crude product was crystallized to give 2.2 g of 4-carboethoxy-1-(p-methoxyphenyl)-3-(N-methyltrifluoroacetamido)azetidine-2-one, m.p. 102°–104°.

NMR (CDCl$_3$): δ 7.2 (d, J=9, 2H), 6.75 (d, J=9, 2H), 5.5 (d, J=6, 1H), 4.7 (d, J=6, 1H), 4.2 (q, J=7, 2H), 3.7 (s, 3H), 3.2 (br.s., 3H), 1.2 (t, J=7, 3H).

EXAMPLE 12

4-Carboethoxy-3-methoxyazetidin-2-one

To a solution of 1.4 g of 4-carboethoxy-3-methoxy-1-(p-methoxyphenyl)azetidin-2-one in 50 ml acetonitrile at 0° was added a solution of 8.23 g of cerric ammonium nitrate in 50 H$_2$O over 3 minutes. After stirring at 0° for 1 hour the solution was poured into 200 ml of 10% sodium sulfite and extracted with 3×75 ml of ethyl acetate. The combined organic extracts were washed with 10% sodium sulfite and saturated sodium chloride solutions and dried over sodium sulfate. Filtration and evaporation gave an amber oil which was recrystallized from methylene chloride/hexane to give 700 mg of 4-carboethoxy-3-methoxyazetidine-2-one; m.p. 91°–92°.

NMR (CDCl$_3$): δ 7.1 (br.s, 1H), 4.7 (dd, J$_1$=2, J$_2$=5, 1H), 4.3 (d, J=5, 1H), 4.15 (q, J=7, 2H), 3.4 (s, 3H), 1.25 (t, J=7, 3H).

Following substantially the same procedure as described in Example 12 but using an appropriate 3-substituted azetidinone compounds (a)–(f) were prepared:

(a) 4-Carboethoxy-3-chloroazetidin-2-one

NMR (CDCl$_3$): 67 7.3 (br.s., 1H), 5.0 (dd, J$_4$=2, J$_2$=6, 1H), 4.4 (d, J=6, 1H), 4.2 (q, J=7, 2H), 1.3 (t, J=7, 3H).

(b) 4-Carboethoxy-3-phenylazetidin-2-one-2-(cis and trans)

NMR (CDCl$_3$): δ cis: 7.2 (s, 5H), 6.4 (br.s., 1H), 4.7 (d, J=6, 1H), 4.4 (d, J=6, 1H), 3.7 (q, J=7, 2H), 0.75 (t, J=7, 3H); trans: 7.2 (s, 5H), 6.9 (br.s, 1H), 4.3 (br.d, J=2, 1H), 4.1 (q, J=7, 2H), 4.0 (d, J=2, 1H), 1.2 (t, J=7, 3H).

(c) 4-Carboethoxy-3-(N-methyltrifluoroacetamido)azetidin-2-one

NMR (CDCl$_3$): δ 7.2 (br.s., 1H), 5.4 (d, J=6, 1H), 4.5 (d, J=6, 1H), 4.15 (q, J=7, 2H), 3.2 (s, 3H), 1.2 (t, J=7, 3H).

(d) 4-Carboethoxy-3-vinylazetidin-2-one (cis and trans)

NMR (CDCl$_3$) cis: δ 7.1 (br.s., 1H), 5.2–5.8 (m, 3H), 4.0–4.4 (m, 4H), 1.25 (t, J=7, 3H); trans: δ=7.25 (br.s., 1H), 5.0–6.2 (m, 3H), 4.1 (q, J=7, 2H), 3.9 (d, J=2, 1H), 3.7 (dd, J$_1$=2, J$_2$=7, 1H), 1.2 (t, J=7, 3H).

(e) 4-Carboethoxy-3-ethylazetidin-2-one

Cis: NMR (CDCl$_2$): δ 6.9 (br.s., 1H); 4.2 (m, 3H); 3.4 (dd, J$_1$=6, J$_2$=8, 1H); 1.51 (q, J=8, 2H); 1.2 (t, J=7, 3H); 1.0 (t, J=8, 3H).

Trans: NMR(CDCl$_3$): δ 6.8 (br.s., 1H); 4.2 (q, J=7, 2H); 3.8 (d, J=2, 1H); 3.2 (dd, J$_1$=2, J$_2$=7, 1H); 1.8 (dq, J$_1$=2, J$_2$=8, 2H); 1.2 (t, J=7, 3H); 1.0 (t, J=8, 3H).

(f) 3-Azido-4-carboethoxyazetidin-2-one

EXAMPLE 13

4-Carboethoxy-3-(N-methyltrifluoroacetamido)azetidine-2-one-1-sulfonic acid tetrabutylammonium salt To a solution of 140 mg of 4-carboethoxy-3-(N-methyltrifluoroacetamido)azetidine-2-one in 5 ml of pyridine at 80° was added 250 mg of sulfur trioxide pyridine complex, and the resulting mixture was stirred for 30 minutes at 80°. The solution was poured into 100 ml of 0.5N KH$_2$PO$_4$ and extracted with 2×25 ml of methylene chloride. The combined organic washes were back-extracted with 25 ml of KH$_2$PO$_4$ solution. The combined aqueous phases were then treated with 680 mg of tetrabutylammonium hydrogen sulfate and extracted with 3×50 ml of methylene chloride. After drying (sodium sulfate) and evaporation of the organic phase the crude 4-carboethoxy-3-(N-methyltrifluoroacetamido)azetidine-2-one-1-sulfonic acid tetrabutylammonium salt was chromatographed to yield pure as an oil.

NMR (CDCl$_3$): δ 5.3 (d, J=6, 1H), 4.7 (d, J=6, 1H), 4.15 (q, J=7, 2H), 3.2 (m, 11H), 0.8–1.8 (m, 31H).

Applying the same procedure as described above, the following tetrabutylammonium salts of other azetidine derivatives were prepared:

(a) 4-Carboethoxy-3-methoxyazetidin-2-one-1-sulfonic acid tetrabutylammonium salt NMR (CDCl$_3$): δ 4.55 (d, J=6, 1H), 4.5 (d, J=6), 4.1 (q, J=7, 2H), 3.4 (s, 3H), 3.2 (m, 8H), 0.8–1.8 (m, 31H).

(b) 4-Carboethoxy-3-vinylazetidin-2-one-1-sulfonic acid tetrabutylammonium salt

EXAMPLE 14

4-Carboethoxy-1-(p-nitrobenzenesulfonyl)-3-phenylazetidin-2-one

To a solution of 720 mg of 4-carboethoxy-3-trans-phenylazetidin-2-one in 20 ml methylene chloride at 0° were added sequentially 595 mg of p-nitrobenzenesulfonyl chloride and 0.48 ml of DBU. The solution was stirred for several hours, diluted with 50 ml of methylene chloride, washed once with water and dried over sodium sulfate. Filtration and evaporation gave a crude residue which was chromatographed to yield pure 4-carboethoxy-1-(p-nitrobenzenesulfonyl)-3-phenyl-azetidin-2-one.

NMR (CDCl$_3$): δ 8.3 (d, J=9, 2H), 8.2 (d, J=9, 2H), 7.2 (br.s., 5H), 4.0 (q, J=7, 2H), 3.7 (m, 2H), 1.2 (t, J=7, 3H). Similarly prepared was the corresponding cis-3-phenyl compound. NMR (CDCl$_3$): δ 8.4 (d, J=9, 2H), 8.25 (d, J=9, 2H), 7.2 (s, 5H), 5.0 (s, 1H), 3.7 (m, 3H), 0.85 (t, 5=7, 3H).

Following the same procedure as described above but using appropriate reagents, the following compounds were prepared:

(a) 4-Carboethoxy-1-(p-nitrobenzenesulfonyl)-3-vinylazetidin-2-one

NMR (CDCl$_3$): δ cis, 8.3 (d, J=9, 2H), 8.2 (d, J=9, 2H), 5.2–6.0 (m, 3H), 4.0–4.6 (m, 4H), 1.2 (t, J=7, 3H); trans: δ 8.2 (d, J=9, 2H), 8.15 (d, J=9, 2H), 5.2–6.0 (m, 3H), 3.9–4.4 (m, 4H), 1.25 (t, J=7, 3H).

(b) 4-Carboethoxy-3-ethyl-1-(p-nitrobenzenesulfonyl)azetidin-2-one (c) 3-Azido-4-carboethoxy-1-(p-nitrobenzenesulfonyl)azetidin-2-one (d) 4-Carboethoxy-3-chloro-1-(p-nitrobenzenesulfonyl)azetidin-2-one

EXAMPLE 15

4-Carboethoxy-3-phenyl-1-trifluoromethanesulfenylazetidin-2-one

To a mixture of 1.2 g of 4-carboethoxy-3-phenylazetidin-2-one and 1.2 ml of triethylamine in 25 ml of methylene chloride at 0° was added dropwise over 10 minutes 11.25 ml of a 10% solution of trifluoromethanesulfenyl chloride in ether. After stirring for several hours the solution was washed with water, dried over sodium sulfate, filtered and evaporated. The crude residue was chromatographed to yield pure 4-carboethoxy-3-phenyl-1-trifluoromethanesulfenylazetidin-2-one as an oil.

NMR (CDCl$_3$): δ 7.2 (s, 5H), 4.6 (d, J=3, 1H), 4.3 (m, 3H), 1.3 (t, J=7, 3H).

EXAMPLE 16

1-Tosyloxymethyl-3-n-Propyl-4-p-nitrophenylthioazetidin-2-one

Step A: Preparation of 3-Propyl-4-p-nitrophenylthio azetidin-2-one

3-Propyl-4-acetoxy azetidinone, 171 mg, is refluxed with 200 mg p-nitrophenyl thiol in 10 ml benzene for 6 hours. The solution is washed 3x with aqueous Na$_2$CO$_3$, dried with MgSO$_4$, filtered and evaporated. The residue is chromatographed on silica gel, eluting with 10:1 CHCl$_3$-EtOAc, affording 3-propyl-4-p-nitrophenylthioazetidin-2-one.

Step B: Preparation of 1-Tosyloxymethyl-3-n-propyl-4-p-nitrophenylthio azetidin-2-one 3-Propyl-4-p-nitrophenylthioazetidine-2-one, 266 mg, is stirred overnight at room temperature with 0.25 ml aqueous formalin (37%) and 17 mg K$_2$CO$_3$, Water and formaldehyde are removed in vacuo, and flushed with 2 ml pyridine. The residue is taken up in 4 ml pyridine and treated for 1 hour at room temperature with 200 mg p-toluenesulfonyl chloride. The pyridine is evaporated and replaced with 5 ml benzene. The solution is washed with aqueous H$_3$PO$_4$ and then aqueous K$_2$HPO$_4$, dried with MgSO$_4$, filtered and evaporated. The residue is chromatographed on silica gel, eluting with 25:1 CHCl$_3$-EtOAc, providing 1-tosylmethyl-3-n-propyl-4-p-nitrophenylthio-azetidin-2-one.

EXAMPLE 17

1-Tosyloxymethyl-3-n-propyl-4-p-nitrophenylsulfinyl azetidin-2-one

1-Tosyloxymethyl-3-n-propyl-4-p-nitrophenylsulfinylazetidin-2-one, 450 mg, is treated for ½ hour in 10 ml CH$_2$Cl$_2$ with 172 mg m-chloroperbenzoic acid. The solution is washed with aqueous K$_2$HPO$_4$, dried with MgSO$_4$, filtered and evaporated, leaving pure 1-tosyloxymethyl-3-n-propyl-4-p-nitrophenylsulfinyl azetidin-2-one.

EXAMPLE 18

1-Acetoxymethyl-4-p-nitrophenylsulfinyl-3-n-propylazetidin-2-one

Step A: Preparation of 3-n-propyl-4-p-nitrophenylthioazetidin-2-one 3-n-Propyl-4-azetoxyazetidinone (1.164 g, 6.58 mmole) and 1.02 g (6.58 mmole) p-nitrothiophenol were heated in a tube in the steam bath for 3.5 hours. The reaction mixture was cooled, diluted with 100 ml ethyl acetate, and the organic phase was washed with 100 ml water, 70 ml 1M H$_3$PO$_4$ and 3×100 ml saturated K$_2$CO$_3$. The organic phase was dried over magnesium sulfate, filtered, and solvent removed in vacuo to yield 1.53 g of yellow crystals which were chromatographed on a silica gel column in chloroform-ethyl acetate (4:1) to give 359 mg (19%) of 3-n-propyl-4-p-nitrophenylthioazetidin-2-one.

NMR (CDCl$_3$): δ 0.92 (tr, 3H), 1.2–1.6 (br m, 4H), 3.10 (tr, 1H), 4.91 (d, 1H), 7.0 (br s, 1H), 7.50 (d, 2H), 8.20 (d, 2H).

Step B: Preparation of
1-Acetoxymethyl-4-p-nitrophenylthio-3-n-propylazetidin-2-one A mixture of 273 mg (0.94 mmol) azetidinone from Step A, 26.3 mg paraformaldehyd and 178 mg (0.56 mmole) cesium carbonate was stirred in 20 ml dry tetrahydrofuran at ambient temperature 16.5 hours under nitrogen. A mixture of 430 μl pyridine and 2.56 ml acetic anhydride was added to the reaction mixture and the stirring continued 5 more hours. The solvents were evaporated in vacuo to give 604 mg crude product which was chromatographed on a silica gel flash column in hexane-ethyl acetate 3/1. This gave 102 mg (30%) of 1-acetoxymethyl-4-p-nitrophenylthio-3-n-propylazetidin-2-one.

NMR (CDCl$_3$): δ 1.0 (tr, 3H), 1.2–1.85 (br m, 4H), 2.1 (s, 3H), 3.22 (tr, 1H), 4.95 (d, 1H), 5.18 (ABBA pattern, J$_1$=30H$_3$, J$_2$=5H$_3$, 2H), 7.65 (d, 2H), 8.22 (d, 2H).

Step C: Preparation of
1-Acetoxymethyl-4-p-nitrophenylsulfinyl-3-n-propylazetidin-2-one To a solution of 46 mg (0.127 mmole) azetidinone from Step B in 4 ml CH$_2$Cl$_2$ and 4 ml saturated aqueous NaHCO$_3$ was added 27 mg (0.127 mM) 80% m-chloroperbenzoic acid and the reaction mixture stirred vigorously 15 minutes. The phases were separated and the organic phase was dried over MgSO$_4$, filtered and stripped to yield 57 mg crude product which was chromatographed on a 1000μ silica gel prep TLC plate in chloroform-ethyl acetate 4:1 to yield 15 mg (31%) of 1-acetoxymethyl-4-p-nitrophenylsulfinyl-3-n-propylazetidin-2-one.

NMR (CDCl$_3$): δ 0.93 (tr, 3H), 1.2–1.8 (br m, 4H), 2.1 (s, 3H), 3.55 (tr, 1H), 4.66 (d, 1H), 5.04 (ABBA pattern, J$_1$=34H$_3$, J$_2$=6H$_3$, 2H), 8.2 (d, 2H), 8.52 (d, 2H).

EXAMPLE 19

4-Acetoxy-3-n-propylazetidin-2-one-1-sulfonic acid tetrabutylammonium salt

A solution of 82 mg (0.463 mmole) 3-propyl-4-acetoxy azetidin-2-one in 5 ml pyridine was heated to 80°. 221 Mg (1.39 mmole) sulfur trioxide-pyridine complex was heated and the reaction mixture stirred at 80° one hour. It was then poured into 100 ml 0.5M KH$_2$PO$_4$ (aqueous) and washed with 2×25 ml CH$_2$Cl$_2$. The combined organic washes were backwashed with 25 ml 0.5M KH$_2$PO$_4$. 157 Mg (0.463 mmole) Bu$_4$N-HSO$_4$ was added to the combined aqueous phases. This was extracted with 2×25 ml CH$_2$Cl$_2$ and the combined extracts were dried over MgSO$_4$, filtered, and stripped in vacuo to yield 12.4 mg of an oily residue which was chromatographed on a small silica gel column, eluted first with 75 ml hexane/ethyl acetate (3:1) to remove starting material, then with 100 ml ethyl acetate/methanol (4:1) to yield 13 mg (5.7%) 4-acetoxy-3-n-propylazetidin-2-one-1-sulfonic acid tetrabutylammonium salt.

NMR (CDCl$_3$): δ 10 (m, 16H), 1.75 (br m, 20H), 2.16 (s, 3H), 2.90 (br s, H), 3.1 (tr, 1H), 3.3 (tr, 8H), 4.08 (br tr, 1H), 6.18 (s, 1H).

What is claimed is:
1. A compound of formula

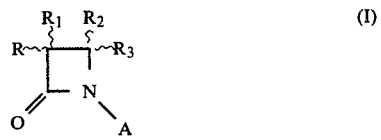

wherein:
R is hydrogen or C$_{1-3}$alkyl;
R$^1$ is
(1) hydrogen;
(2) C$_{1-6}$alkyl;
(3) C$_{1-6}$alkoxy;
(4) C$_{1-6}$alkenyl; or
(5) phenyl or phenyl substituted with one or more radicals selected from the group consisting of loweralkyl, hydroxy, alkoxy, halo, nitro, loweralkylthio, arylthio, mercapto, amino, cyano, carboxy, aminosulfonyl, aminosulfenyl, aminosulfinyl, carbamoyl, carbamoyloxy, loweralkyl or aryl sulfonyl, loweralkyl or aryl sulfinyl, SO$_3$R$^5$, azido, or carboxamido;

R$^2$ is hydrogen;
R$^3$ is
(1) SR$^5$ wherein R$^5$ represents C$_{1-6}$alkyl, phenyl or substituted phenyl as previously defined;
(2) SOR$^5$;
(3) C$_{1-6}$alkanoyloxy;
(4) COOB or CONBB$_1$ wherein B and B$_1$ independently represent
(a) H;
(b) straight or branched alkyl having from 1 to 20 carbon atoms;
(c) aryl having from 6 to 10 carbon atoms;
(d) cycloalkyl having from 3 to 8 carbon atoms;
(e) straight or branched alkenyl having from 2 to 20 carbon atoms;
(f) straight or branched alkynyl having from 2 to 20 carbon atoms;
(g) aralkyl, alkaryl, aralkenyl, aralkenyl, alkenylaryl or alkenylaryl wherein alkyl, aryl, alkenyl and alkynyl are as previously defined; the above groups (a)–(g) can be unsubstituted or can be substituted by one or more selected radicals from the group consisting of loweralkyl, hydroxy, alkoxy, halo, nitro, loweralkylthio, arylthio, mercapto, cyano, carboxy, aminosulfonyl, aminosulfenyl, aminosulfinyl, carbamoyl, carbamyloxy, loweralkyl or aryl sulfonyl, loweralkyl or aryl sulfinyl, SO$_3$R$^5$, azido, amino, or carboxamido;
(5) phenyl or substituted phenyl as previously defined; and
A is
(1) SO$_2$R$^5$; or
(2) SO$_3^-$M$^+$ wherein M$^+$ represents (a) an alkali anion selected from a group consisting of Na$^+$ and K$^+$; or (b) a quaternary ammonium group of formula N$^+$(R$^5$)$_4$.

2. The group of claim 1 wherein the compound is: trans-3-phenyl-4-ethoxycarbonyl-1-p-nitrophenylsulfonylazetidine-2-one.

3. The compound of claim 1 wherein the compound is:
cis-3-phenyl-4-ethoxycarbonyl-1-p-nitrophenylsulfonylazetidine-2-one.

4. The compound of claim 1 wherein the compound is:
   cis-3-(1-propenyl-4-ethoxycarbonyl-1-p-nitrophenyl-sulfonylazetidin-2-one.

5. The compound of claim 1 wherein the compound is:
   cis-4-ethoxycarbonyl-3-n-propyl-1-p-nitro-phenylsulfonylazetidin-2-one.

6. The compound of claim 1 wherein the compound is:
   Trans-4-ethoxycarbonyl-3-ethyl-1-p-methylphenyl-sulfonyl-azetidin-2-one.

7. The compound of claim 1 wherein the compound is:
   trans-4-ethoxycarbonyl-3-ethyl-1-p-methylphenylsulfonylazetidin-2-one.

8. The compound of claim 1 wherein the compound is:
   4-ethoxycarbonyl-3-ethyl-1-p-nitrophenylsulfonylazetidin-2-one.

9. The compound of claim 1 wherein the compound is:
   cis-4-ethoxycarbonyl-1-p-nitrophenylsulfonyl-3-vinylazetidin-2-one.

10. The compound of claim 1 wherein the compound is:
    4-benzyloxycarbonyl-1-p-nitrophenylsulfonylazetidin-2-one.

11. The compound of claim 1 wherein the compound is:
    cis-4-acetoxy-3-n-propylazetidin-2-one-1-sulfonic acid tetra(n-butyl)ammonium salt.

* * * * *